(12) United States Patent
Sellars et al.

(10) Patent No.: US 11,242,293 B2
(45) Date of Patent: Feb. 8, 2022

(54) BIOFERTILIZER FORMULATION FROM ALGAE AND RELATED METHODS

(71) Applicant: Honda Motor Co., Ltd., Tokyo (JP)

(72) Inventors: Daniel T. Sellars, West Liberty, OH (US); Joel W. Agner, Bluffton, OH (US)

(73) Assignee: Honda Motor Co., Ltd., Tokyo (JP)

( * ) Notice: Subject to any disclaimer, the term of this patent is extended or adjusted under 35 U.S.C. 154(b) by 14 days.

(21) Appl. No.: 16/830,592

(22) Filed: Mar. 26, 2020

(65) Prior Publication Data

US 2021/0300833 A1    Sep. 30, 2021

(51) Int. Cl.
| | | |
|---|---|---|
| C05F 11/08 | (2006.01) | |
| C05B 1/04 | (2006.01) | |
| C05C 5/02 | (2006.01) | |
| C05C 9/00 | (2006.01) | |
| C05C 11/00 | (2006.01) | |

(Continued)

(52) U.S. Cl.
CPC ............... C05F 11/08 (2013.01); C05B 1/04 (2013.01); C05C 5/02 (2013.01); C05C 9/005 (2013.01); C05C 11/00 (2013.01); C05D 1/00 (2013.01); C05F 5/002 (2013.01); C05G 1/00 (2013.01); C05G 5/12 (2020.02); C12N 1/12 (2013.01); C12N 1/14 (2013.01)

(58) Field of Classification Search
None
See application file for complete search history.

(56) References Cited

U.S. PATENT DOCUMENTS

| 3,645,040 A | 2/1972 | Ort | |
|---|---|---|---|
| 5,747,416 A * | 5/1998 | McArdle | A23B 4/20 504/115 |

(Continued)

FOREIGN PATENT DOCUMENTS

| CN | 104193500 A | 12/2014 |
|---|---|---|
| EP | 2881380 A1 | 6/2015 |

(Continued)

OTHER PUBLICATIONS

Bhattarai, Surya P., and Durga D. Dhakal. "Opportunities for Recycling of Agricultural Wastes for Manufacturing of High Value Fertilizer for Sustainable Agricultural Industry in Nepal." Skill, Knowledge and Innovation Transfer to Nepal (2014): 30.

(Continued)

*Primary Examiner* — Wayne A Langel
(74) *Attorney, Agent, or Firm* — Plumsea Law Group, LLC

(57) ABSTRACT

A biofertilizer is disclosed that include specific formulations of algae biomass and a mycorrhizal fungus. This biofertilizer may be a useful way of utilizing algae biomass created for carbon sequestration purposes for a productive agricultural purpose. The combination of algae biomass and mycorrhizal fungus may provide advantageous effects to a crop, as the algae may be a nutrient source for both the crop itself and also for the mycorrhizal fungus that allows the fungus to grow and form a mycorrhizal relationship with the root system of the crop. The biofertilizer may be pelletized with rice hull filler and have a specific range of moisture content, so as to be compatible to agricultural fertilizer delivery equipment. Methods of manufacturing the pelletize biofertilizer are also provided.

18 Claims, 6 Drawing Sheets

(51) Int. Cl.
  *C05D 1/00* (2006.01)
  *C12N 1/12* (2006.01)
  *C12N 1/14* (2006.01)
  *C05F 5/00* (2006.01)
  *C05G 5/12* (2020.01)
  *C05G 1/00* (2006.01)

(56) References Cited

U.S. PATENT DOCUMENTS

| | | | |
|---|---|---|---|
| 10,173,936 B2 | 1/2019 | Fiato et al. | |
| 10,900,013 B2* | 1/2021 | Krivov | C12M 47/10 |
| 2008/0236227 A1* | 10/2008 | Flynn | A01C 21/00 |
| | | | 71/7 |
| 2012/0144887 A1* | 6/2012 | Fiato | C12M 43/06 |
| | | | 71/7 |
| 2013/0316903 A1* | 11/2013 | Hughes | C05D 9/00 |
| | | | 504/102 |
| 2014/0051131 A1* | 2/2014 | Dodd | C12N 1/36 |
| | | | 435/101 |
| 2014/0345341 A1* | 11/2014 | Fiato | C10G 1/083 |
| | | | 71/7 |
| 2015/0045215 A1* | 2/2015 | Devine | C05F 17/00 |
| | | | 504/101 |
| 2016/0115432 A1 | 4/2016 | Dahiya | |
| 2016/0355445 A1* | 12/2016 | Bobeck | C05F 11/08 |
| 2018/0223246 A1 | 8/2018 | Shinde et al. | |
| 2019/0337864 A1* | 11/2019 | Asada | B01J 2/28 |

FOREIGN PATENT DOCUMENTS

| | | |
|---|---|---|
| KR | 101575805 B1 | 12/2015 |
| WO | 2013055887 A1 | 4/2013 |
| WO | 2018144965 A1 | 8/2018 |

OTHER PUBLICATIONS

Google Machine Translation of CN Patent No. 104193500 A.
Google Machine Translation of KR Patent No. 101575805 B1.

* cited by examiner

BIOFERTILIZER FORMULATION FROM ALGAE AND RELATED METHODS

BACKGROUND

The present disclosure relates to the field of agricultural biofertilizers and their manufacture. In particular, this disclosure relates to algae based biofertilizers that may be used to enhance crop productivity.

Agricultural fertilizers are widely used to promote crop growth—for staple crops such as wheat, corn, cotton, soybeans, and many others. Generally, fertilizers deliver nutrients to soil, that allow a crop to better grow and develop in that soil. Fertilizers include organic fertilizers, that are derived from living organisms, such as animal manure or compost. Fertilizers may also be artificial in nature, created through chemical processes such as nitrogen fertilizers made through the Haber-Bosch process. A wide range of fertilizer formulations are known in the art of agricultural sciences.

Additionally, the use of algae as part of fertilizer formulations is known in the art. Algae biomass may be used for a wide variety of applications, including fertilizers, biofuels, bioplastics, and many others. Algae biomass is also considered an excellent way to reduce net carbon emissions, as its high growth rate can efficiently absorb large amounts of carbon dioxide.

In this way, there is a need in the art for ways to best utilize algae biomass after it has sequestered carbon dioxide. Conventional uses for large amounts of algae biomass, such as biofuels, may not always be economical in view of changing energy market conditions. At the same time, existing algae based fertilizers may not best promote crop growth and may not integrate well with existing agricultural infrastructure.

Accordingly, there is a need in the art for improved algae based biofertilizer formulations.

SUMMARY

In one aspect, this disclosure provides a biofertilizer comprising: algae biomass; and a mycorrhizal fungus; wherein algae biomass comprises between 50.0 and 70.0 weight percent of the biofertilizer, and the mycorrhizal fungi comprises between 1.0 and 2.0 weight percent of the biofertilizer.

In another aspect, this disclosure provides a pelletized biofertilizer comprising: algae biomass comprising between 50.0 and 70.0 weight percent of the biofertilizer; a mycorrhizal fungus comprising between 1.0 and 2.0 weight percent of the biofertilizer; an organic filler comprising between 25.0 and 49.0 weight percent of the biofertilizer; and nutrients, including a nitrogen source, a phosphorus source, and a potassium source; wherein the pellets are configured to be compatible with agricultural fertilizer delivery equipment.

In still another aspect, a method for manufacturing a pelletized biofertilizer is provided, the method comprising: receiving an algae biomass slurry; mixing into the slurry a mycorrhizal fungus; mixing into the slurry an organic filler; extruding the slurry through an extruder; pelletizing the slurry with a pelletizer; and drying the pellets.

Other systems, methods, features and advantages of the invention will be, or will become, apparent to one of ordinary skill in the art upon examination of the following figures and detailed description. It is intended that all such additional systems, methods, features and advantages be included within this description and this summary, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DETAILED DESCRIPTION

Figure 1:
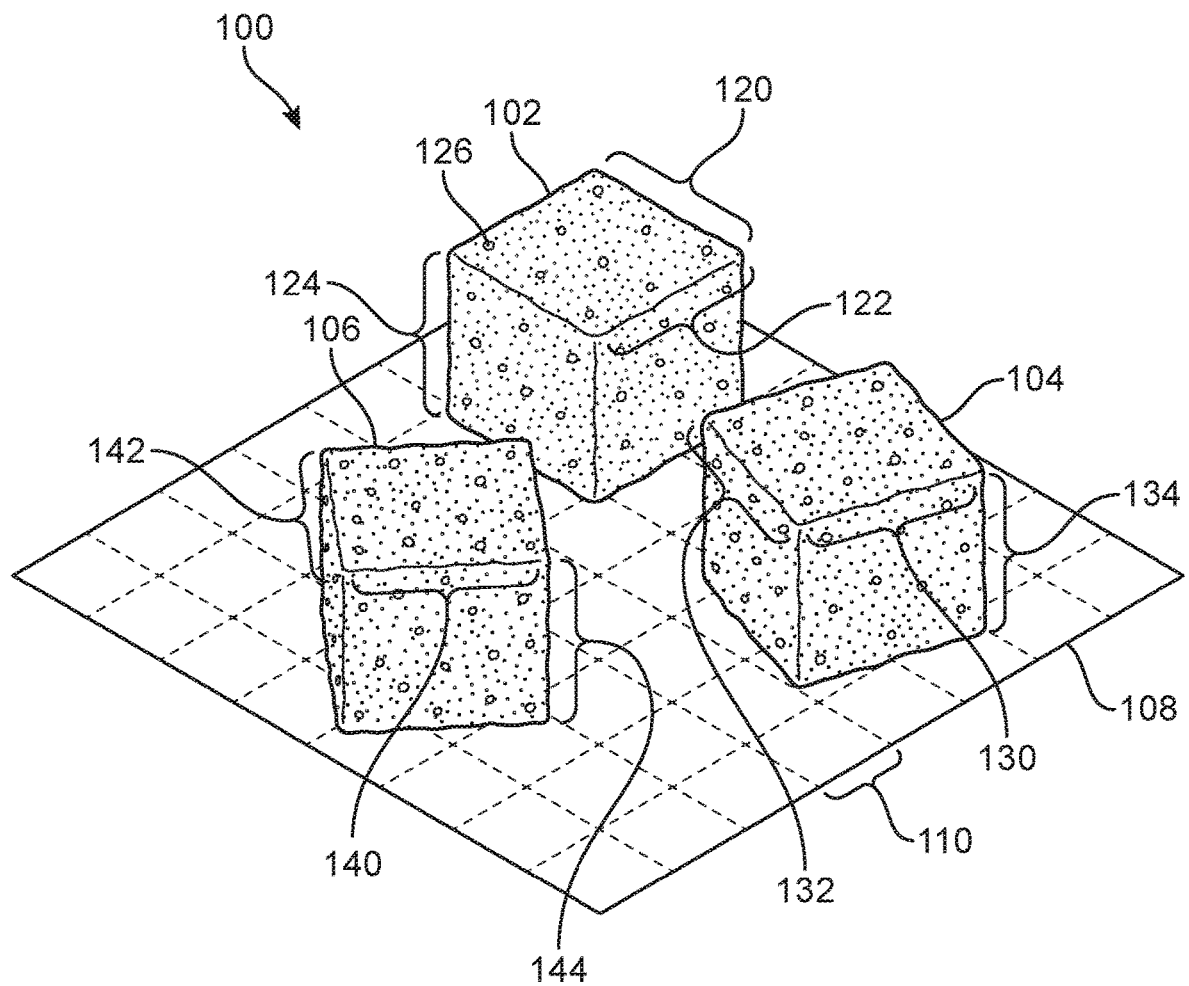
FIG. 1 is a diagram of several biofertilizer pellets in accordance with this disclosure.

An algae based biofertilizer and associated method of manufacture are described herein. According to the techniques of the example embodiments, the algae based biofertilizer may be used to promote crop growth while having sequestered carbon dioxide.

As used here, a fertilizer may be any composition that enhances plant crop growth when applied to either soil or plant tissues. Fertilizers may include materials of both natural origin and also materials of synthetic origin. In particular, a biofertilizer may be a substance which contains living microorganisms that act as a fertilizer by increasing the supply or availability of nutrients to the plant.

In various embodiments of this disclosure, a biofertilizer may include algae biomass. The algae biomass used in a biofertilizer herein may include any of a variety of well known photosynthetic eukaryotic algae organisms, including both single cell algae and multi-cellular algae. Example types of algae may include *Chlorella, Botryococcus, Chlamydomonas*, Spirogyra, and many others.

The biofertilizer may further include a mycorrhizal fungus in conjunction with the algae biomass. A mycorrhizal fungus may be any species of fungus capable of forming a mycorrhiza symbiotic relationship between the fungus and a plant. In a mycorrhizal relationship, the fungus colonizes the host plant's root tissues and provides increased soil water and nutrient uptake to the plant in exchange for sugars produced by the plant. Specifically, a mycorrhizal fungus may extend the plant's root absorptive area, giving it access to nutrients it would otherwise not be able to attain.

Mycorrhizal fungi generally may include endomycorrhizal fungi and ectomycorrhizal fungi. Endomycorrhizal fungi generally may grow at least partially intracellularly, while ectomycorrhizal fungi may generally grow extracellularly. Examples of a mycorrhizal fungus may include *Glomus intraradices, Glomus mosseae, Glomus aggrega-*

*tum, Glomus etunicatum, Glomus deserticola, Rhizopogon villosulus, Rhizopogon luteolus, Rhizopogon amylopogon, Rhizopogon fulvigleba*, and *Pisolithus tinctorius*.

Generally, the combination of algae biomass and a mycorrhizal fungus may provide synergistic advantages to the crop onto which the biofertilizer is applied. For example, the algae may be beneficial for the plant's growth by providing nutrients contained in the algae biomass. The mycorrhizal fungus may promote increased soil water and nutrient uptake, as mentioned. Together in the biofertilizer, the mycorrhizal fungus may amplify the benefits of the algae by using the algae as a food source that promotes growth of the mycorrhizal fungus. In this way, the mycorrhizal fungus (as a living microorganism) may consume at least a portion of the algae biomass when the biofertilizer is exposed to appropriate growing conditions such as exposure to water and sunlight. As a result, the crop may receive increased nutrients and water both directly from the algae biomass—and also from the mycorrhizal fungus that has successfully colonized its root system due to the presence of the algae biomass that also promotes the growth of the mycorrhizal fungus.

In particular embodiments, the algae biomass and mycorrhizal fungus may be present in particular weight ranges. For example, the algae biomass may be present in the biofertilizer in an amount of greater than 50.0% by weight, or greater than 60.0% by weight, or from 50.0% to 70.0% by weight, or from 50.0% to 60% by weight, or about 66% by weight. In this way, the algae biomass may be the major component of the biofertilizer. The mycorrhizal fungus may be present in the biofertilizer in an amount of from 1.0% to 2.0% by weight, or about 1.5% by weight.

The biofertilizer may further include additional ingredients, such as additional nutrients including one or more of a nitrogen (N) source, a phosphorus (P) source, and a potassium (K) source. These ingredients may be artificial, created through chemical processes. Generally, these nutrients are referred to in agricultural science as "NPK" nutrients. Example nitrogen sources may include ammonia, ammonium sulfate, ammonium nitrate, calcium ammonium nitrate, urea, and others known in the art. Example phosphorus sources may include single superphosphate, triple superphosphate, diammonium phosphate, monoammonium phosphate, ground rock phosphate, and others known in the art. Example potassium sources may include potassium hydroxide, potassium carbonate, potassium chlorate, potassium chloride, potassium nitrate, potassium sulfate, potassium permanganate, and other known in the art. The presence of additional NPK nutrients in the biofertilizer may further aid the growth of the crop.

In some embodiments, the biofertilizer may further include fillers. Fillers may refer to materials that affect the consistency and other bulk properties of the biofertilizer without significantly adding nutrients. Fillers may generally be non-reactive with any other ingredients in the biofertilizer. In particular embodiments, the biofertilizer may contain an organic filler. Organic fillers may include any filler material originating from an animal or plant source. Example fillers may include sand, limestone, sawdust, ground corn cobs, and rice hulls. In particular, rice hulls may be used as an organic filler that may provide advantageous physical bulk properties to the biofertilizer, while still being biodegradable.

A filler may be present in the biofertilizer in an amount of from 25.0% by weight to 49.0% by weight. In particular embodiments, a filler may be about 33% by weight of the biofertilizer. The presence of fillers, and in these amounts, may contribute to the biofertilizer achieving compatibility with agricultural fertilizer delivery equipment by ensuring that the biofertilizer has sufficient durability as discussed below.

Next, the biofertilizer may be made into the form of pellets. As is generally known in the art, pellets may refer to agglomerations of individual ground ingredients, or mixtures of such ingredients—as is commonly used for a variety of agricultural uses. A pelletized biofertilizer may be compatible with standard agricultural equipment for spreading fertilizers, as discussed below with respect to FIG. 4.

In particular embodiments of a biofertilizer, the biofertilizer may be a pelletized biofertilizer having a certain mechanical durability. Durability of the pellets may help ensure that the pellets may be compatible with agricultural fertilizer delivery equipment. Specifically, durability may ensure that the pellets can be dispersed evenly across a field so that all crops receive approximately the same coverage of the biofertilizer. Pellets lacking in such durability may also unduly crumble, causing some portion of the biofertilizer to go to waste instead of being spread where needed on a crop field. In some embodiments, durability of the pellets may be measured according to ASABE Standard S269.5. This standard is promulgated by the American Society of Agricultural and Biological Engineers (ASABE), and includes several tests for measurement of agricultural pellets including methods and procedures for measuring unit specific density, bulk density, durability, and moisture content. For durability, this standard uses a tumbler device to measure a ratio of mass left in the tumbler after tumbling to an original mass of the pellets. Pelletized biofertilizers according to this embodiment may, in some embodiments, have durability according to this standard of at least 70%, or at least 80%, or at least 90%. Pelletized biofertilizers having such a minimum durability may be more compatible with agricultural fertilizer delivery equipment, in that the pellets will not unduly crumble prior to spreading.

Referring now to FIG. 1, this figure shows an example of several pellets 100 of a pelletized biofertilizer according this disclosure. Pellets 100 may include first pellet 102, second pellet 104, and third pellet 106. As shown, each of the pellets 100 may be substantially cubical in shape. However, in other embodiments not shown, pelletized biofertilizer in accordance with this disclosure may have other pelletized shapes such as rectangular, cylindrical, and others.

As shown in FIG. 1, first pellet 102 may have first width 120, first depth 122, and first height 124. Second pellet 104 may have second width 130, second depth 132, and second height 134. Third pellet 106 may have third width 140, third depth 142, and third height 144. In various embodiments, each of first width 120, second width 130, and third width 140 may be substantially equal, or within about 10% of each other, or within about 20% of each other. Similarly, each of first depth 122, second depth 132, and third depth 142 may be substantially equal, or within about 10% of each other, or within about 20% of each other. The same may apply to each of first height 124, second height 134, and third height 144.

Also shown in FIG. 1 is a sizing indicator 108. Sizing indicator 108 may include intervals 110. Intervals 110 may correspond to 1 cm. In such embodiments, pellets 100 shown in FIG. 1 may measure about 2-3 cm per side. More broadly, pellets in accordance with this disclosure may have a size of from about 1 cm$^3$ to about 9 cm$^3$. This size range may be particularly suited for use in agricultural fertilizer delivery equipment.

Each of pellets 100 may include a main component of algae biomass, such as algae biomass 126 in first pellet 102.

Figure 2:
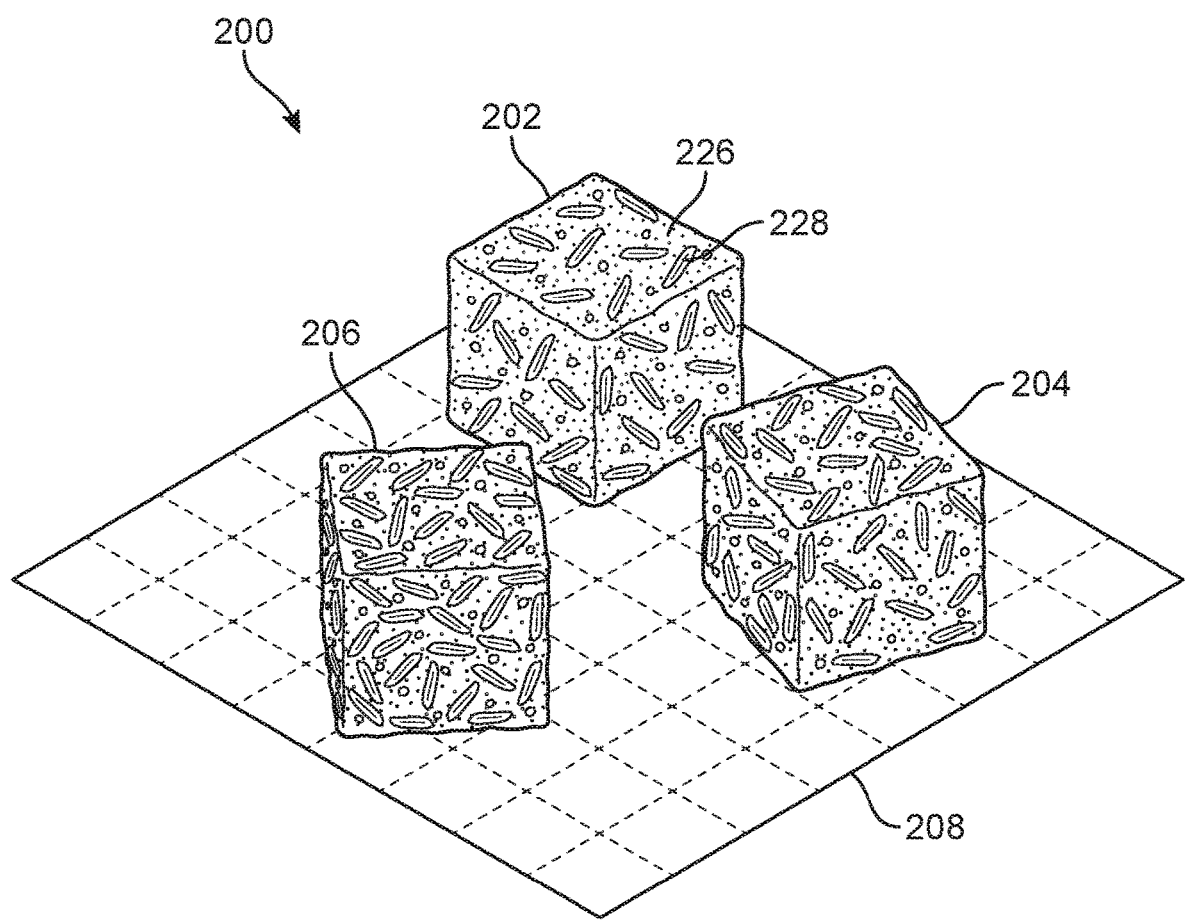
FIG. 2 is a diagram of several biofertilizer pellets containing an organic filler in accordance with this disclosure.

Alternatively, as shown in FIG. 2, each of pellets 200 may include algae biomass portion 226 and also filler 228 as shown with respect to first pellet 202. Second pellet 204 and third pellet 206 may include similar compositions as first pellet 202. Filler 228 may be any filler discussed above, or may in particular embodiments be rice hulls.

Figure 3:
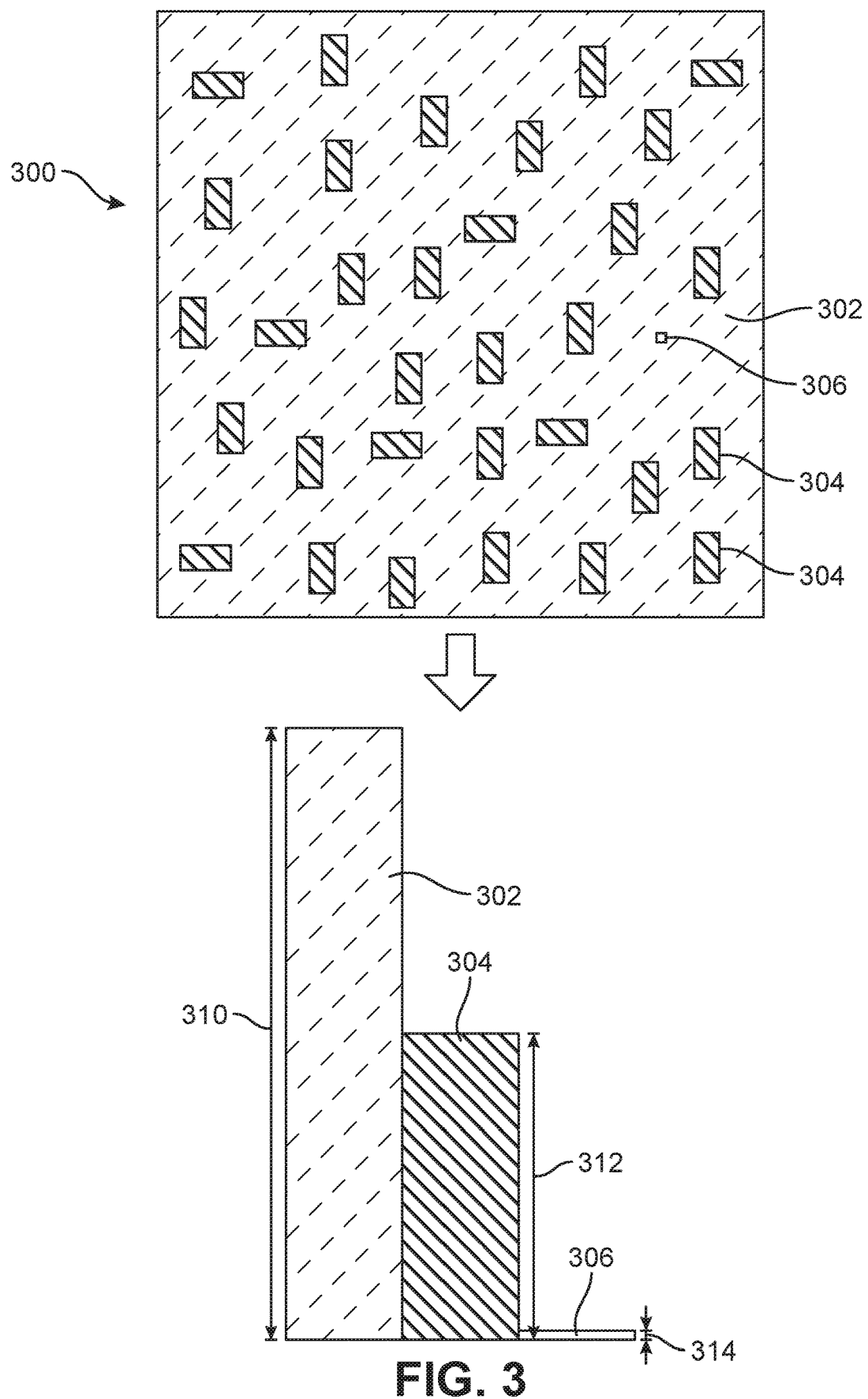
FIG. 3 is a schematic showing relative proportions of ingredients in one embodiment of a biofertilizer in accordance with this disclosure.

FIG. 3 is a schematic showing the relative weight proportions of several ingredients in one embodiment of a pellet 300 of a pelletized biofertilizer. In this particular embodiment, a first ingredient 302 may have a first relative proportion 310. First ingredient 302 may be algae biomass. Next, second ingredient 304 may have a second relative proportion 312. Second ingredient 304 may be a filler such as rice hulls. As shown, second relative proportion 312 may be approximately half of first relative proportion 310. Finally, third ingredient 306 may have a third relative proportion 314. Third ingredient 306 may be a mycorrhizal fungus. Third relative proportion 314 may be approximately ⅓₃ of second relative proportion 312. In this way, schematic 300 shows one embodiment wherein algae biomass may be 66% by weight, rice hulls may be 33% by weight, and mycorrhizal fungus may be 1% by weight.

Figure 4:
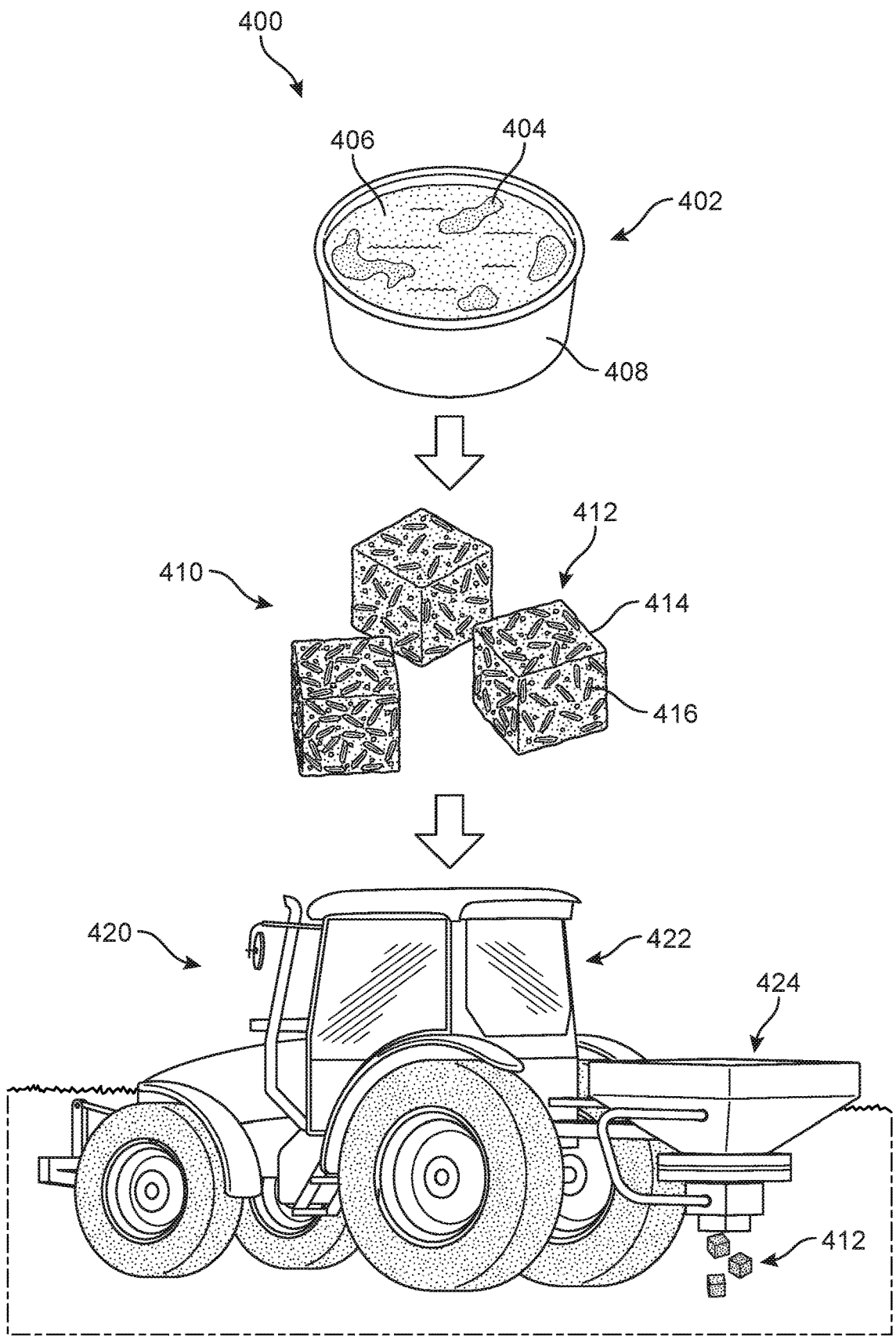
FIG. 4 shows a lifecycle process of how algae biomass may be grown, converted into a biofertilizer in accordance with this invention, and then spread onto crops using conventional agricultural equipment.

Next, FIG. 4 shows a diagram of a lifecycle 400 of how an algae biomass is grown and used. Specifically, algae biomass 404 may be grown in liquid medium 406 held in vat 408 at step 402. In some embodiments not shown, vat 408 may be incorporated in a carbon dioxide sequestration system. Such a sequestration system may, for example, be used to reduce net carbon emissions from a factory or other facility. Next, at step 410 the algae biomass 404 may be formulated with other ingredients as discussed above such that pellets 412 include algae portion 414 and rice hull filler portion 416. The biofertilizer formulation may then be pelletized as discussed below with respect to FIG. 6 to form pellets 412.

Finally, FIG. 4 shows step 420 of using agricultural equipment 422, 424 to spread the pelletized biofertilizer 412 on a crop field. In particular, a tractor 422 may pull a no-till drill fertilizer box 424 that spreads pellets 412. No-till drill fertilizer boxes are well known in the art of agricultural science. Example no-till drill fertilizer boxes (not necessary as shown in FIG. 4) may include the John Deere 1590 model, or the Great Plains 3P606NT mounted no-till compact drill. As discussed above, pelletized biofertilizer in accordance with this disclosure may be compatible with such known agricultural fertilizer delivery equipment. By being compatible with widely used equipment, pelletized biofertilizers may reduce costs to deploy and increase the value and return on investment as compared to other types of known fertilizers.

EXAMPLES

Figure 5:
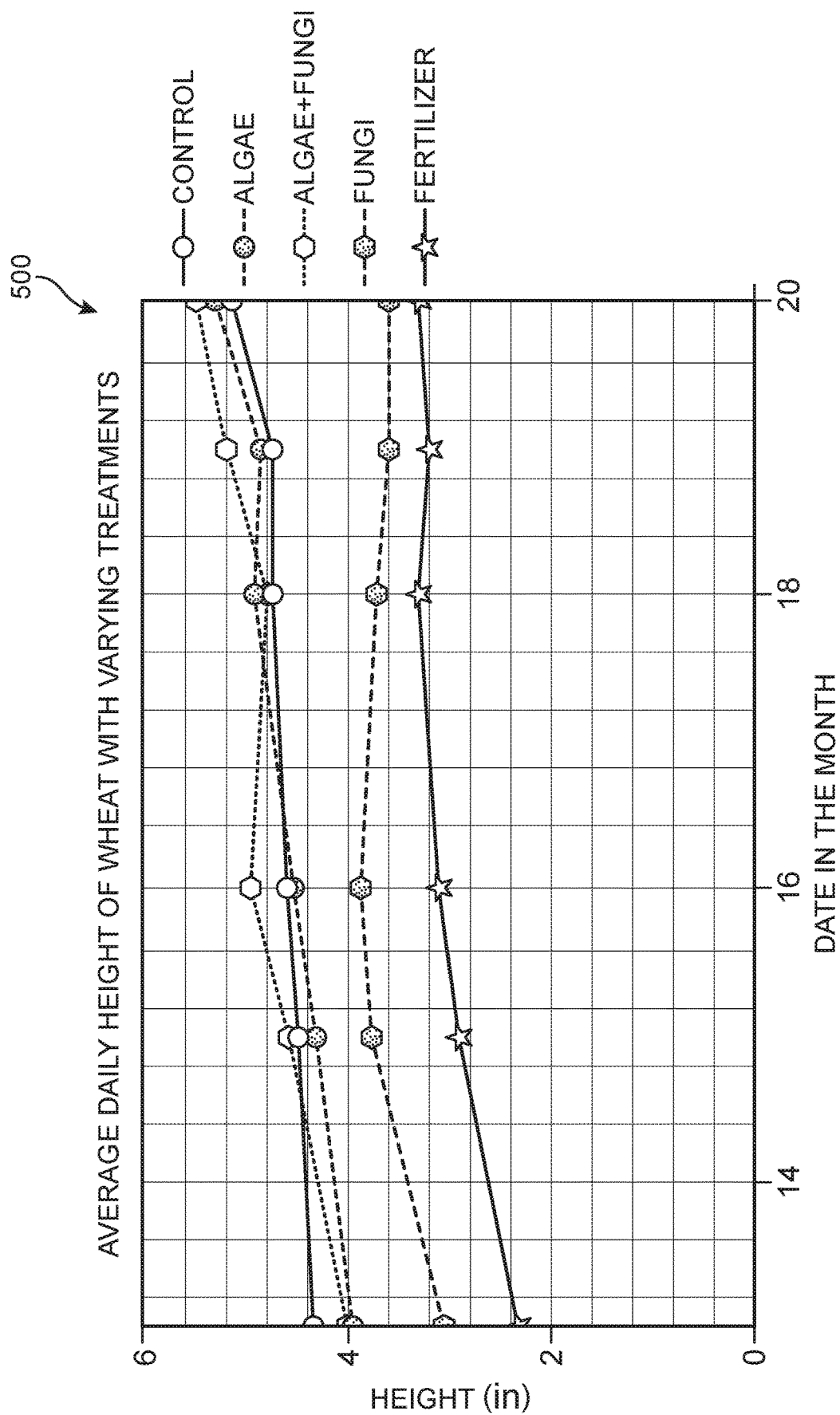
FIG. 5 shows a line chart of growth over time using an example of a biofertilizer in accordance with this disclosure as compared to several comparative examples.

FIG. 5 shows results from an experiment run to evaluate the effectiveness of a biofertilizer composition according to this disclosure as compared to several comparative examples. Namely, each treatment formulation was applied to a serious of wheat plants grown in a greenhouse under otherwise identical growing conditions. The heights of the wheat plants was measured at six times over the course of a 20 day period. The heights were averaged for each example and comparative example to arrive at an average daily height.

The example included a formulation including algae biomass and mycorrhizal fungi, as shown in Table 1 below. The comparative examples included: a control with no treatment, a treatment with only algae biomass, a treatment with only mycorrhizal fungus, and a treatment with a standard known NPK fertilizer. As shown in FIG. 5, the example that included treatment with both algae biomass and mycorrhizal fungus achieved the best growth as measured by height on day 20.

TABLE 1

| Component | "Algae only" | "Algae + Fungi" | "Algae + Fungi + NPK" |
|---|---|---|---|
| Algae biomass | 0.667 | 0.657 | 0.536 |
| Triple superphosphate | 0.00 | 0.00 | 0.137 |
| Potassium nitrate | 0.00 | 0.00 | 0.208 |
| Mycorrhizal fungus | 0.00 | 0.015 | 0.012 |
| Urea | 0.00 | 0.00 | 0.107 |
| Rice hulls | 0.333 | 0.328 | 0.00 |

Table 1 above shows the relative weight proportions of each ingredient. The results of the "algae only" comparative example is shown in FIG. 5, as are the results of the "algae+fungi" example. The "algae+fungi+NPK" example is an example of a formulation in accordance with this disclosure, however no results for this particular formulation are shown in FIG. 5.

Method of Manufacture

Figure 6:
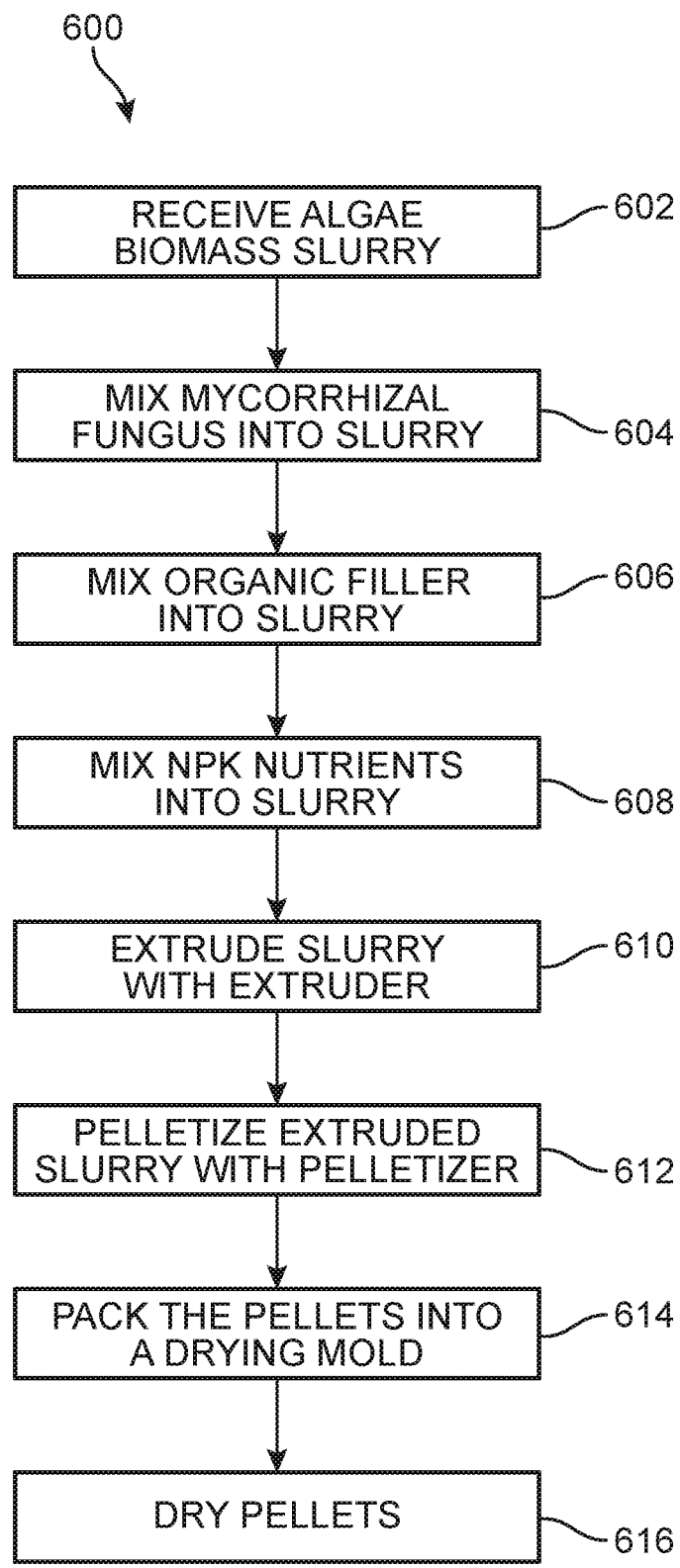
FIG. 6 shows a flowchart of a method of manufacturing a biofertilizer in accordance with this disclosure.

Finally, FIG. 6 shows a flowchart of a method 600 of manufacturing a pelletized biofertilizer in accordance with this disclosure.

Generally, method 600 may include a first step 602 of receiving an algae biomass slurry. Algae biomass slurry may be cultured as shown in FIG. 4 in vat 408, or in other comparable algae cultivation equipment. Next, method 600 may include step 604 of mixing a mycorrhizal fungus into the algae biomass slurry. Step 604 may include precautions to ensure that the mycorrhizal fungus remains alive, so that it can subsequently grow into the root system of the crop to which the biofertilizer is applied.

Step 606 of may be an optional step of mixing organic filler into the slurry. As discussed above, not all biofertilizer formulations in accordance with this disclosure include fillers. Similarly, step 608 may be an optional step of mixing NPK nutrients into the slurry. Generally, steps 604, 606, and 608 may introduce the respective ingredients in amounts sufficient to arrive at the proportions discussed variously above with respect to the final pelletized biofertilizer.

Next, step 610 of process 600 may include extruding the slurry with an extruder. A variety of industrial extruders are known in the art of agricultural science and bulk material processing. Then at step 612 the extruded slurry may be pelletized with a pelletizer. In some embodiments of process 600, steps 610 and 612 may occur substantially simultaneously in a machine designed to both extrude and pelletize the slurry at the same time.

Step 614 may be an optional step of packing the pellets into a drying mold. A drying mold used in step 614 may be a silicone mold. Finally, step 616 may include drying the pellets. In particular, drying step 616 may be performed in order to achieve a desired final moisture content. Moisture content may affect the biofertilizer in several ways, such as by affecting the durability and also by ensuring that harmful mold growth does not occur. In particular embodiments, step 616 may include drying the pellets to a final wet basis moisture content of from 6.0% and 10.0% by weight. Moisture content above these values may allow harmful mold growth, but moisture content below these values may degrade durability.

Accordingly, process 600 may produce pelletized biofertilizer in accordance with any of the embodiments discussed herein.

While various embodiments of the invention have been described, the description is intended to be exemplary, rather than limiting and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

The invention claimed is:

1. A biofertilizer comprising:
   algae biomass;
   a mycorrhizal fungus; and
   an organic filler;
   wherein algae biomass comprises between 50.0 and 70.0 weight percent of the biofertilizer, and the mycorrhizal fungus comprises between 1.0 and 2.0 weight percent of the biofertilizer;
   wherein the biofertilizer has a wet basis moisture content of between 6.0 and 10.0 weight percent; and
   wherein the pellets have a mechanical durability according to ASABE Standard S269.5 of at least 70%.

2. The biofertilizer according to claim 1, wherein the biofertilizer is pelletized into pellets, and the pellets are configured to be compatible with agricultural fertilizer delivery equipment.

3. The biofertilizer according to claim 1, the biofertilizer is pelletized into pellets, the pellets having a size of from about 1 cm$^3$ to about 9 cm$^3$ and being substantially cubical in shape wherein each dimension is within 10% of each other dimension.

4. The biofertilizer according to claim 1, further wherein the organic filler comprises between 25.0 and 49.0 weight percent of the biofertilizer.

5. The biofertilizer according to claim 1, wherein the organic filler includes rice hulls comprising between 25.0 and 49.0 weight percent of the biofertilizer.

6. The biofertilizer according to claim 1, further comprising nutrients including a nitrogen source, a phosphorus source, and a potassium source.

7. The biofertilizer according to claim 1, wherein the mycorrhizal fungus is selected from the group consisting of: *Glomus intraradices, Glomus mosseae, Glomus aggregatum, Glomus etunicatum, Glomus deserticola, Rhizopogon villosulus, Rhizopogon luteolus, Rhizopogon amylopogon, Rhizopogon fulvigleba*, and *Pisolithus tinctorius*.

8. The biofertilizer according to claim 1, wherein the mycorrhizal fungus is live in the biofertilizer, such that the mycorrhizal fungus consumes the algae biomass upon exposure to appropriate growing conditions.

9. The biofertilizer according to claim 1, wherein the algae biomass is derived from an algae including from the group consisting of Chlorella, Botryococcus, Chlamydomonas, and Spirogyra, and mixtures thereof.

10. The biofertilizer according to claim 1, wherein
    the algae biomass comprises about 66 weight percent of the biofertilizer;
    the mycorrhizal fungus comprises about 1 weight percent of the biofertilizer; and
    the organic filler comprises about 33 weight percent of the biofertilizer.

11. A pelletized biofertilizer comprising:
    algae biomass comprising between 50.0 and 70.0 weight percent of the biofertilizer;
    a mycorrhizal fungus comprising between 1.0 and 2.0 weight percent of the biofertilizer;
    an organic filler comprising between 25.0 and 49.0 weight percent of the biofertilizer; and
    nutrients, including a nitrogen source, a phosphorus source, and a potassium source;
    wherein the pellets are configured to be compatible with agricultural fertilizer delivery equipment;
    wherein the biofertilizer has a wet basis moisture content of between 6.0 and 10.0 weight percent; and
    wherein the pellets have a mechanical durability according to ASABE Standard S269.5 of at least 80%.

12. The pelletized biofertilizer according to claim 11, wherein the pellets have a size of from about 1 cm$^3$ to about 9 cm$^3$.

13. The pelletized biofertilizer according to claim 11, wherein the pellets have a mechanical durability according to ASABE Standard S269.5 of at least 90%.

14. The pelletized biofertilizer according to claim 11, wherein:
    the mycorrhizal fungus is live in the biofertilizer, such that the mycorrhizal fungus consumes the algae biomass upon exposure to appropriate growing conditions; and
    the mycorrhizal fungus is selected from the group consisting of: *Glomus intraradices, Glomus mosseae, Glomus aggregatum, Glomus etunicatum, Glomus deserticola, Rhizopogon villosulus, Rhizopogon luteolus, Rhizopogon amylopogon, Rhizopogon fulvigleba*, and *Pisolithus tinctorius*.

15. The pelletized biofertilizer according to claim 11, wherein the pellets have a size of from about 1 cm$^3$ to about 9 cm$^3$ and are substantially cubical in shape wherein each dimension is within 10% of each other dimension.

16. The pelletized biofertilizer according to claim 11, wherein:
    the nitrogen source is urea;
    the phosphorus source is triple superphosphate; and
    the potassium source is potassium nitrate.

17. The pelletized biofertilizer according to claim 11, wherein the algae biomass is derived from an algae including Chlorella, Botryococcus, Chlamydomonas, and Spirogyra.

18. The pelletized biofertilizer according to claim 11, wherein the organic filler is selected from the group consisting of sand, limestone, sawdust, ground corn cobs, and rice hulls.

\* \* \* \* \*